(12) United States Patent
Monk

(10) Patent No.: US 8,912,003 B2
(45) Date of Patent: Dec. 16, 2014

(54) METHODS AND DEVICES FOR DETECTING ISOTHIAZOLONES

(75) Inventor: David James Monk, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 65 days.

(21) Appl. No.: 13/218,500

(22) Filed: Aug. 26, 2011

(65) Prior Publication Data

US 2013/0052744 A1 Feb. 28, 2013

(51) Int. Cl.
*G01N 21/59* (2006.01)
*G01N 21/00* (2006.01)
*G01N 31/22* (2006.01)
*G01N 21/78* (2006.01)

(52) U.S. Cl.
CPC ........... *G01N 31/22* (2013.01); *G01N 21/78* (2013.01)
USPC ............. 436/92; 436/91; 422/50; 422/62

(58) Field of Classification Search
CPC ........ G01N 31/22; G01N 31/00; G01N 21/78
USPC .................................... 436/92, 91
See application file for complete search history.

(56) References Cited

U.S. PATENT DOCUMENTS

| 3,975,155 A | 8/1976 | Geyer |
| 4,110,378 A | 8/1978 | Geyer |
| 4,652,530 A | 3/1987 | Rothman et al. |
| 5,094,957 A | 3/1992 | Willingham |
| 5,554,542 A | 9/1996 | Willingham et al. |
| 7,238,532 B1 * | 7/2007 | Philbrook ........................ 436/92 |
| 7,807,473 B2 * | 10/2010 | Potyrailo et al. .............. 436/164 |

FOREIGN PATENT DOCUMENTS

WO W09404917 A1 3/1994

OTHER PUBLICATIONS

US 5,514,563, 5/1996, Tully et al. (withdrawn).
Barman et al., "The Effects of pH on the Degradation of Isothiazolone Biocides", Tribology International, vol. 25, Issue 4, pp. 281-287, 1992.
Search Report and Written Opinion from corresponding EP Application No. 12181176.4-2204 dated Nov. 30, 2012.

* cited by examiner

*Primary Examiner* — Christine T Mui
(74) *Attorney, Agent, or Firm* — Mary Louise Stanford

(57) ABSTRACT

Methods for quantitative determination of the presence of isothiazolone compounds in a solution include controlling pH of the solution in a range from about 3 to about 10, combining a known quantity of the pH-adjusted solution with a known quantity of an aromatic thiolate anion, quantitatively determining color intensity of the resultant combined solution; and correlating the color intensity with amount of isothiazolone compounds. The methods may be used in automated systems, including systems utilizing optical sensor devices.

13 Claims, 1 Drawing Sheet

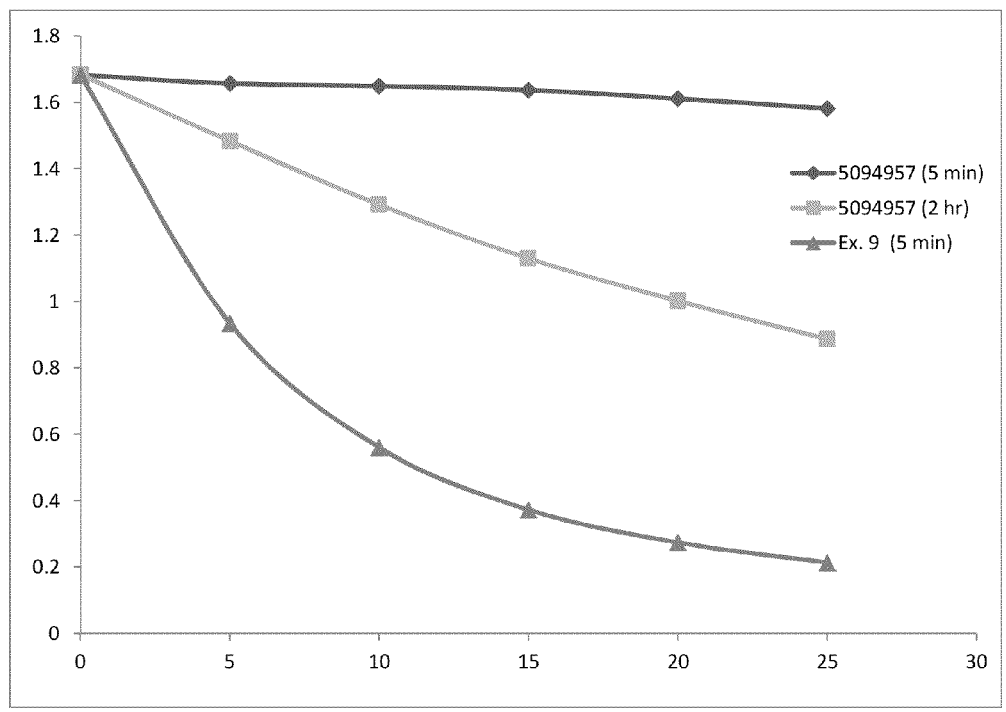

METHODS AND DEVICES FOR DETECTING ISOTHIAZOLONES

BACKGROUND

Isothiazolone (ITA) compounds are commonly used as biocides and preservatives in a variety of aqueous and non-aqueous systems, including cooling tower waters, metalworking fluids, deionized water, and personal care products. Metalworking fluids (MWFs) are used to lubricate and cool a workpiece that is being machined. The fluids include water-free oils, and fluids intended to be diluted with water, including soluble oils; semi-synthetic fluids; and synthetic fluids. Aqueous MWFs can support growth of microbes, introducing contaminants such as cells and cell components, along with related byproducts such as endotoxins, exotoxins, and mycotoxins. The ITA-based biocides added to reduce microbial growth have their own hazardous properties, especially dermatitis (skin rash).

There is a need to determine the concentration of the biocide on demand to enable operators of cooling towers, metal working fluids and other aqueous systems to make economical decisions in the field concerning the timing and need for the addition of biocide to their systems The concentration determination needs to be performed rapidly and accurately both in the field and in the lab, without the need for complicated equipment such as HPLC and with minimal sample preparation. In addition, it would be advantageous to have a concentration determination that can be automated to minimize analyst training and enable automated feedback loops (i.e., automated measure and dose).

Attempts have been made to develop a rapid, reliable and sensitive method for determining the concentration of isothiazolones in aqueous systems for use in field applications. These techniques have been less than satisfactory because of the length of time required to complete the analysis, and susceptibility of the techniques to positive and negative interferences caused by additives and ionic impurities commonly found in aqueous systems, and because of the difficulty in obtaining a high degree of sensitivity for measuring low concentrations of isothiazolones. Various additives are typically added to recirculating cooling tower water to prevent or inhibit the precipitation of hardness ions, to disperse scale, and to combat corrosion. For example, polyacrylates, phosphates, phosphonates, iron, zinc, tin and other metals are commonly found in cooling tower water as well as suspended particulate materials such as clay and silt.

U.S. Pat. No. 5,094,957 describes a colorimetric assay for determination of isothiazolone concentration. However, the assay requires hours for color development, and do not reach a minimum value within that time period. Therefore, there remains a need for a method to determine ITA concentration that can be performed in less than 20 minutes, with minimal sample preparation, and is amenable to automation.

BRIEF DESCRIPTION

Accordingly, in one aspect, the present invention relates to methods for quantitative determination of the presence of isothiazolone compounds in a solution. The methods include controlling pH of the solution in a range from about 3 to about 10, combining a known quantity of the pH-adjusted solution with a known quantity of an aromatic thiolate anion, quantitatively determining color intensity of the resultant combined solution, and correlating the color intensity with amount of isothiazolone compounds.

In another aspect, the present invention relates to automated systems for quantitative determination of the presence of isothiazolone compounds in a solution.

In yet another aspect, the present invention relates to sensor devices for quantitative determination of the presence of isothiazolones in a solution. The sensor device includes substrate and a hydrogel sensor film that includes an aromatic thiolate reagent or anion.

DRAWINGS

These and other features, aspects, and advantages of the present invention will become better understood when the following detailed description is read with reference to the accompanying drawings in which like characters represent like parts throughout the drawings, wherein:

FIG. 1 is a graph comparing an embodiment of a method of the present invention to the assay of U.S. Pat. No. 5,094,957.

DETAILED DESCRIPTION

Isothiazolones that may be detected using the methods of the present invention include substituted and unsubstituted 3-isothiazolones and mixtures of these. Examples include 5-chloro-2-methyl-3-isothiazolone (CMI) and 2-methyl-3-isothiazolone (MI). A 3/1 mixture of CMI to MI designated as KATHON®, available from Dow (Rohm & Haas), is widely used as a biocide. Some isothiazolones present in aqueous systems may be in the form of complexed magnesium or calcium salts.

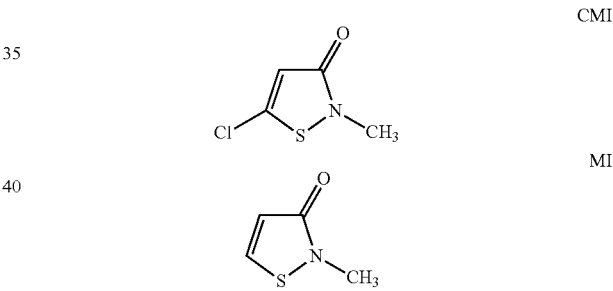

In the context of the present invention, the term "isothiazolone compounds" means one or more substituted or unsubstituted 3-isothiazolone compounds or complexes. That is, the term encompasses a single ITA compound, in addition to mixtures of ITA compounds and complexes.

Solutions that may be analyzed using the methods of the present invention include the water-based metal working fluids, such as synthetic, semi-synthetic fluids, and soluble oils, cooling tower waters, and other waters that are subject to industrial water treatment. The method can be used to determine the presence of ITA in the solutions, as well as quantitatively determine the concentration of the isothiazolone compounds in the range from greater than 0 ppm to less than about 100 ppm, particularly from greater than 0 ppm to less than about 30 ppm, and more particularly from greater than 0 ppm to less than about 5 ppm. The methods may be automated, and may be conveniently incorporated into industrial water treatment systems, including systems for management of metal working fluids.

Aromatic thiolate anions that may be used in the methods or assays of the present invention are colored materials that change color upon combination with the ITA. The aromatic thiolate anions include thionitrobenzoate salts, thiopyridine salts, and thionicotinic salts. Specifically, salts of 5-thio-2-nitrobenzoate, 2-thiopyridine salts, 4-thiopyridine salts, and 6-thionicotinoate salts may be used. Ellman's reagent, 5,5'-dithiobis(2-nitrobenzoate) may be used to generate the 5-thio-2-nitrobenzoate (TNB) anion upon cleavage of the S—S bond. The TNB anion may be formed by reacting the aromatic thiolate reagent with a nucleophilic agent, including basic compounds such as NaOH, and nucleophilic compounds such as sodium phenyl thiolate.

In some embodiments, the pH of the solution to be analyzed is controlled in the range from about 3 to about 9, particularly from about 4 to about 9. At pH lower than about 3, absorption of the aromatic thiolate anion may be insufficient for quantitative determination of a change upon combination with the isothiazolones. At pH greater than about 9, the time period for the color change is significantly greater than the desirable twenty minutes, and absorbance may not reach a constant value. For example, in some embodiments, pH for analysis of metalworking fluids is about 8.

The thiolate anion may be present or formed in a basic solution having a concentration of hydroxide ion ranging from about 0.03N to 0.6N, more particularly from about 0.03N to 0.1N. In many embodiments, it is desirable to buffer either the aromatic thiolate anion solution or the sample solution, or both, in order to maximize stability of the analytical system. The sample solution may be buffered prior to combination with the aromatic thiolate anion solution. For example, when analyzing for ITA in deionized water, it may desirable to buffer with 0.1N phosphate buffer at a pH of about 7, specifically 7.3.

Color intensity may be determined by visual inspection, or by measuring absorbance of the solution using a spectrophotometric device in the range from about 275 nm to about 510 nm, particularly at about 400 nm. Maximum absorbance of the TNB anion is about 412 nm; the term 'about 400 nm' includes 412 nm. Other aromatic thiolate salts may have a different absorption maximum.

For the methods of the present invention, color intensity may be determined after a time period as short as five minutes. More generally, the time period may be less than about twenty minutes. Longer time periods may also be used, if desired. For example, for MWFs analyzed at pH 8.2, the color change was complete after about 20 minutes.

In a particular embodiment, a method according to the present invention includes controlling pH of the solution in a range from about 3 to about 9, combining a known quantity of the pH-controlled solution with a known quantity of thionitrobenzoate anion, after a time of less than about 20 minutes, measuring absorbance of the resulting solution at about 400 nm, and correlating absorbance of the solution with the amount of isothiazolone compounds.

Methods according to the present invention can be automated in many ways. In particular, the methods can be performed using an optical sensor device. Accordingly, in one embodiment, methods of the present invention include measuring absorbance at about 400 nm of a hydrogel sensor film of a sensor device, contacting the film with a known amount of the solution, measuring the absorbance of the resulting film at about 400 nm, and correlating a change in absorbance of the film with an amount of isothiazolones in the solution. The hydrogel sensor film includes an aromatic thiolate anion or an aromatic thiolate reagent that can be reacted to produce an aromatic thiolate anion. In some embodiments, sensors that include a substrate and sensing element comprising a sensing matrix, as described in U.S. Pat. No. 7,651,663, may be used.

Sensor devices according to the present invention include a substrate and a hydrogel sensor film that includes an aromatic thiolate anion or reagent, particularly 5,5'-dithiobis(2-nitrobenzoate) or an aromatic thiolate anion derived therefrom. Sensor device structures suitable for use in the sensor devices of the present invention, as well as materials suitable for use in the substrate and hydrogel sensor films of the devices, methods suitable for preparing sensor devices of the present invention, and procedures that may be used for reading the sensor devices are disclosed in U.S. Pat. No. 7,170,609, U.S. Pat. No. 7,456,968, U.S. Pat. No. 7,524,455, U.S. Pat. No. 7,651,663, U.S. Pat. No. 7,807,473, and U.S. Pat. No. 7,977,660, each assigned to the General Electric Company, the entire contents of each of which is incorporated herein by reference. Other sensor devices for use with the methods of the present invention may be based on analytical systems using surface-functionalized microspheres.

EXAMPLES

General: Preparation of Solutions 0.1 M Aqueous Sodium Phosphate Buffer, pH 7.27
  Add 6.9 g sodium phosphate monobasic (CAS 10049-21-5) to 400 mL DI water. Add 0.19 g EDTA disodium salt dihydrate (CAS 6381-92-6). Adjust pH to 7.27 with hydrochloric acid or sodium hydroxide. Dilute to 500 mL with DI water.
5,5'-Dithiobis(2-nitrobenzoic acid) (DTNB) Stock in 0.01M pH 7.27 Buffer (4000 ppm)
  Dissolve 4 mg DTNB in 1 mL 0.1M aqueous sodium phosphate pH 7.27 buffer. Store at 0° C.
2.4 M Sodium Hydroxide
  Dilute 1.1 g 50% sodium hydroxide to 10.0 g with DI water.
DTNB Working Solution (500 ppm)
  Add 125 uL 4000 ppm DTNB Stock to 875 uL DI water. Add 30 uL of 2.4 M sodium hydroxide and allow to sit for 15 minutes before use (the solution will turn bright yellow.) The solution was optimized to produce maximum absorbance in minimum time, and was stable for at least 3 weeks in refrigerator.

Example 1

DTNB Working Solution Optimization

DTNB working solution was prepared by adding 125 uL 4000 ppm DTNB Stock to 875 uL DI water and then adding various quantities & concentrations of sodium hydroxide to achieve a range of final sodium hydroxide concentrations (0.0036 M, 0.0105 M, 0.0310 M, 0.0708 M, 0.128 M, 0.186 M, 0.368 M, and 0.546 M)

For each solution, immediately after adding sodium hydroxide and thoroughly mixing, a 125 uL aliquot was added to 2.21 mL of 7.5% Castrol Syntilo 9904 in water with no isothiazolone. pH of the Castrol Syntilo 9904 was adjusted to 8.2 before adding the DTNB working solution. The absorbance of the resulting solution was measured at 412 nm in 5 minute increments for 30 minutes to observe the reaction rate (measured as the initial absorbance) and stability (defined as absorbance change over time.)

The concentration of sodium hydroxide used to split DTNB to TNB anion affected both the reaction rate and stability. Initial (1 minute) absorbance increased with increasing sodium hydroxide concentrations until 0.186 M. Concentrations above that exhibited the same initial absorbance, meaning that the reaction has proceeded to completion.

Choice of a concentration near or at the maximum enable the rapid use of freshly prepared DTNB working solutions and speeds up the overall assay.

Lower sodium hydroxide concentrations (0.0036 M, 0.0105 M, 0.0310 M) resulted in solutions with increasing absorbance over time. Such an increase is undesirable, as it would negatively impact the assay results. Higher sodium hydroxide concentrations (0.128 M, 0.186 M, 0.368 M, and 0.546 M) resulted in solutions with decreasing absorbance over time. Such a decrease is undesirable, as it would negatively impact the assay results. Therefore, 0.708 M was chosen as the optimal sodium hydroxide concentration, as the reaction achieves completion in just over 1 minute and the solution is stable over time with no increase or decrease in absorbance.

Example 2

DTNB Working Solution Optimization Experiment (Part 2)

DTNB working solutions of various sodium concentrations were prepared as in Example 1. Immediately after adding sodium hydroxide and thoroughly mixing the solution, a 125 uL aliquot was added to 2.21 mL of 7.5% Castrol Syntilo 9904 in water with 10 ppm isothiazolone (pH adjusted to 8.2 before addition). The absorbance of the resulting solution was measured at 412 nm in 5 minute increments for 30 minutes to observe the overall absorbance change and stability.

The concentration of sodium hydroxide used to split DTNB to TNB anion affected the overall absorbance change. The total absorbance change increased with decreasing concentration until 0.708 M. Higher sodium hydroxide concentrations (0.128 M, 0.186 M, 0.368 M, and 0.546 M) resulted in a smaller total absorbance change. Lower sodium hydroxide concentrations (0.0036 M, 0.0105 M, 0.0310 M) resulted in total change in absorbance that were lower than that of the 0.0708 M solution. Higher sodium hydroxide concentrations (0.186 M, 0.368 M, and 0.546 M) resulted in solutions with increasing absorbance after 20 minutes. Since the concentration range of interest was 0-20 ppm, 0.708 M was chosen as the optimal final sodium hydroxide concentration, as it achieved the greatest difference for a 10 ppm isothiazolone solution.

Example 3 pH Optimization (Part 1)

DTNB working solution was prepared by adding 30 uL 2.43 M sodium hydroxide (final conc. 0.0708 M) to 125 uL 4000 ppm DTNB Stock in 875 uL DI water. 7.5% Castrol Syntilo 9904 in water with no ITA was prepared, and separate 125 mL aliquots were adjusted to pH 7.31 and 9.27 using HCl or NaOH as required.

A 125 uL aliquot of DTNB working solution was added to 2.21 mL of 7.5% Castrol Syntilo 9904 in water with no isothiazolone. The absorbance of the resulting solution was measured at 412 nm in 5 minute increments for 30 minutes to observe the initial absorbance change and stability.

Very little difference was observed at pH 7.31 and 9.27. For pH 7.31, the absorbance dropped 0.01 Absorbance unit, but remained stable over 30 minutes. For pH 9.27, the absorbance decreased 0.02 absorbance units, but remained relatively stable over 30 minutes. Since these represented the two pH extremes, no other pHs were tested.

Example 4 pH Optimization (Part 2)

DTNB working solution was prepared by adding 30 uL 2.43 M sodium hydroxide (final conc. 0.0708 M) to 125 uL 4000 ppm DTNB Stock in 875 uL DI water. 7.5% Castrol Syntilo 9904 in water was prepared, and separate 125 mL aliquots were pH adjusted to 7.31, 7.93, 8.45, 8.96, 9.27, and 9.58. A 125 uL aliquot of DTNB working solution was added to 2.21 mL of 7.5% Castrol Syntilo 9904 in water with 10 ppm isothiazolone. The absorbance of the resulting solution was measured at 412 nm in 5 minute increments for 30 minutes to observe the overall absorbance change and stability.

It was observed that the total absorbance change increased with decreasing pH. Higher pH (9.27 and 9.58) resulted in solutions with increasing absorbance after 20 minutes. Such an increase is undesirable, as it could negatively impact the assay results. Lower pH (7.31, 7.93, 8.45) resulted in solutions with decreasing absorbance after 20 minutes. A pH of 8.96 gave a relatively stable result from 20 minutes to at least 30 minutes. A pH of ~8.2 yielded a reasonable color change at 20 minutes that was relatively stable. That pH was also close to that of the solutions being measured, which was convenient for pH adjustment. Therefore, pH 8.2 was selected for use in other experiments.

It should be noted that a different pH may be desirable for other concentration ranges (higher pH for higher concentrations and lower pH for lower concentrations). The assay in the range of 1-20 ppm could be completed in as little as 5 minutes if it was reasonable to adjust the pH to 7.3.

Example 5

The response curves at various pH were recorded to find the optimal pH to maximize the color change and achieve a rapid assay. Phosphate buffer (1.0 M) was prepared and 30 mL aliquots were adjusted to pH of 3, 4, 5, 6, 7, 8, 9, 10, 11, and 12. KATHON® 886 MW biocide was added to a semi micro cuvette followed by 2.065 mL of one of the above phosphate buffers to yield a 10 ppm solution. The solution was mixed and allowed to stand for one minute. DTNB working solution (130 uL) was added, the solution was thoroughly mixed, and the absorbance of the solution was measured at 412 nm in 5 minute increments for 2 hours.

pH affected the overall absorbance change and how fast the change occurred. The magnitude of the color change was greatest between pH 3 and 10, and the maximum change was between pH 5 and 7. The color change was much faster at pH between 3 and 9 than it was above pH 10. The fastest color change occurred at pH 7 to 8—the maximum absorbance was obtained in just 5 minutes.

Above pH 10, the magnitude of the change in absorbance was greater than at lower pH, but the time to achieve the full color change was significantly longer than 25 minutes.

Example 6

Solutions containing 0, 5, 10, 15, 20 and 25 ppm isothiazolinone were analyzed at pH 4, 5, 6, 7, 8, and 9 to generate response curves. 1.0 M Phosphate buffer was prepared and 30 mL aliquots were adjusted to pH 4, 5, 6, 7, 8, and 9. KATHON® 886 MW (11.1 uL, 22.2 uL, 33.3 uL, 44.4 uL, or 55.5 uL of 1000 ppm) was added to a semimicro cuvette followed by 2.065 mL of one of the phosphate buffers. The solution was mixed and allowed to stand for one minute. These preparations resulted in final isothizolinone concentrations of 5, 10, 15, 20, 25 ppm. DTNB working solution (130 uL) was added, the solution was thoroughly mixed, and the absorbance of the solution was measured at 412 nm after 5 minutes.

At pH between 5 and 7, the largest color change for concentrations in the range of 0-15 ppm isothiazolinone (ITA) was produced. The largest change was at pH 6 for the range of 0-5 ppm ITA. Since the dynamic range of the assay changes with pH, adjusting the pH can allow the same concentration of DTNB to be used to analyze various ITA concentration ranges.

Example 7

Stability of Isothiazolinones 1.0 M Phosphate buffer was prepared and 30 mL aliquots were adjusted to the following pHs: 3, 7, 10, and 12. 22.2 uL of 1000 ppm KATHON® 886 MW biocide was added to a semi micro cuvette followed by 2.065 mL of one of the above phosphate buffers. These preparations resulted in a final isothiazolinone concentration 10 ppm. The solution was mixed and allowed to stand for one minute before measuring the absorbance spectrum from 250 nm to 500 nm. Additional spectra were obtained until no notable change between subsequent spectra was observed.

The KATHON® biocide appeared to be stable at pHs between 3 and 10. It exhibited a wavelength of maximum absorbance of approximately 274 nm. In addition, the molar absorptivity appeared to be constant across this range of pHs. The isothiazolones did not appear to be stable at a pH of 12. The wavelength of maximum absorbance changed from 274 nm to 304 nm after the first five minutes and then shifted back to 274 nm. In addition, a small peak at 398 nm appeared and grew over time.

Example 8

The spectrum of DTNB added to 10 ppm ITA was analyzed versus time at various pHs to evaluate the color change mechanism. 1.0 M Phosphate buffer was prepared and 30 mL aliquots were adjusted to the following pHs: 3, 7, 10, and 12. 22.2 uL of 1000 ppm KATHON® 886 MW was added to a semi micro cuvette followed by 2.065 mL of one of the above phosphate buffers. The solution was mixed and allowed to stand for one minute. These preparations resulted in a final isothiazolinone concentration 10 ppm.

DTNB working solution (130 uL) was added, the solution was thoroughly mixed, and the absorbance spectrum from 250 nm to 500 nm was measured every five minutes. The corresponding absorbance spectrum of the ITA was subtracted from each spectrum to accentuate change in the TNB and isothiazolinone regions.

At pH 7, the TNB anion absorbance ($\lambda$max: ~412 nm) rapidly decreased with a corresponding increase in the TNB region (275-350 nm, $\lambda$max: ~314 nm). No change was observed in the region where isothiazolinone absorbs (250-310 nm, $\lambda$max: ~275 nm). As such, it is likely the isothiazolinone structure did not change. At pH 12, the TNB anion absorbance ($\lambda$max ~412 nm) slowly decreased without a corresponding increase in the TNB peak (275-350 nm, $\lambda$max: ~314 nm). The absorbance increased in the region where isothiazolinone absorbs (250 nm to 350 nm, $\lambda$max 275 nm). This suggests the isothiazolinone structure changed.

The color change mechanism at pH 7 is different than that at pH 12. This difference likely results in the rapid nature of the assay of the present invention. It is possible that at pH7, isothiazolinone catalytically converts TNB- to TNB, while at pH 12, isothiazolinone reacts directly with TNB—.

Comparative Example 1

U.S. Pat. No. 5,094,957, Example 1

A 500 ppm solution of DTNB was prepared in 1:1 methanol:aqueous sodium phosphate (0.01M) pH 8.0 buffer. A drop of 50% NaOH was added to convert the DTNB to TNB anion. This solution was bright yellow. 0.130 mL of the solution was mixed with 2.065 mL of the analyte solutions to yield a final TNB concentration of 30 ppm. Absorbance readings were taken at 400 nm after 2 hr on 0, 5, 10, 15, 20, and 25 ppm KATHON® 886 (prepared from a 1000 ppm stock solution in DI Water). Samples could be visually differentiated. The pH of the solution was 11.4.

Comparative Example 2

U.S. Pat. No. 5,094,957 Example 2

Experiment 2 as described in U.S. Pat. No. 5,094,957 was performed as written: a 500 ppm solution of 5,5'-dithiobis(2-nitrobenzoic acid) (DTNB) was prepared in a 1/1 solution of methanol/aqueous sodium phosphate (0.01M) pH 8.0 buffer. A drop of 50% NaOH was added to convert DTNB to 5-thio-2-nitrobenzoate (TNB) anion. This solution is bright yellow. The solution was mixed with analyte solutions to yield a final TNB concentration of approximately 30 ppm.

Absorbance readings were taken at 400 ppm after 2 hr on several concentrations of isothiazolone (ITA). It was found that the absorbance decreased continuously over the course of the experiment (~23 hours). It should be noted that the patent incorrectly states that the absorbance reaches a minimum value in 12 hours. However, Table 2 shows that absorbance decreased over the entire 24-hour time of the experiment.

Example 9

Assay Procedure for Isothiazolone Determination

A sample containing KATHON® 886 MW was filtered through a 0.45 μm Teflon filter to remove oil and particulates. The pH was adjusted to 8.20, and 2.085 mL of the sample was added to a clean vial. DTNB working solution (125 μL) was added to the sample solution. After about 20 minutes, absorbance at 412 nm was measured.

Example 10

The assay procedure of Example 9 was compared to the assay of Comparative Example 1 (U.S. Pat. No. 5,094,957), for solutions containing from 0 to 25 ppm isothiazolinone. The response after five minutes was compared to the 5 minute and 2 hour responses of Comparative Example 1. Results are illustrated in the graph of FIG. 1. The assay of Example 9 produced a greater response in 5 minutes than that of the assay of Comparative Example in either 5 minutes or two hours.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for quantitative determination of the presence of isothiazolone compounds in a solution, said method comprising
controlling pH of the solution in a range from 3 to 10;
combining a known quantity of the pH-adjusted solution with a known quantity of an aromatic thiolate anion in a basic solution having a concentration of hydroxide ion ranging from 0.03N to 0.6N;
quantitatively determining color intensity of the resultant combined solution; and
correlating the color intensity with amount of isothiazolone compounds;
wherein color intensity reaches a minimum value after less than 20 minutes and is stable for at least 30 minutes thereafter.

2. A method according to claim 1, wherein the color intensity is determined after less than five minutes.

3. A method according to claim 1, wherein the pH of the solution is controlled in a range from 4 to 9.

4. A method according to claim 1, wherein the aromatic thiolate anion is derived from 5,5'-dithiobis(2-nitrobenzoate).

5. A method according to claim 1, wherein the concentration of the isothiazolone compounds in the solution ranges from greater than 0 ppm to less than 100 ppm.

6. A method according to claim 1, wherein the concentration of the isothiazolone compounds in the solution ranges from greater than 0 ppm to less than 30 ppm.

7. A method according to claim 1, wherein the concentration of the isothiazolone compounds in the solution ranges from greater than 0 ppm to less than 5 ppm.

8. A method according to claim 1, wherein the aromatic thiolate anion is present in a basic solution having a concentration of hydroxide ion ranging from 0.04N to 0.061N.

9. A method according to claim 1, wherein the step of quantitatively determining color intensity comprises measuring absorbance of the solution in a range from 275 nm to 510 nm.

10. A method according to claim 1, wherein the step of quantitatively determining color intensity comprises measuring absorbance of the solution at 400 nm.

11. A method according to claim 1, wherein the solution is a metal working fluid.

12. A method according to claim 1, comprising
controlling pH of the solution in a range from 3 to 9;
combining a known quantity of the pH-controlled solution with a known quantity of thionitrobenzoate anion;
after a time of less than 20 minutes, measuring absorbance of the resulting solution at 400 nm; and
correlating absorbance of the solution with amount of isothiazolone compounds.

13. An automated system for performing a method according to claim 1.

* * * * *